(12) United States Patent
Crottet et al.

(10) Patent No.: US 7,412,897 B2
(45) Date of Patent: Aug. 19, 2008

(54) DEVICE FOR MEASURING TIBIO-FEMORAL FORCE AMPLITUDES AND FORCE LOCATIONS IN TOTAL KNEE ARTHROPLASTY

(75) Inventors: Denis Crottet, Delley (CH); Ion Petros Pappas, Budapest (HU); Thomas Maeder, La Sarraz (CH); Caroline Jacq, Ecublens (CH); Hannes Bleuler, Buchillon (CH)

(73) Assignee: Synthes (U.S.A.), West Chester, PA (US)

(*) Notice: Subject to any disclaimer, the term of this patent is extended or adjusted under 35 U.S.C. 154(b) by 0 days.

(21) Appl. No.: 11/640,515

(22) Filed: Dec. 14, 2006

(65) Prior Publication Data
US 2007/0180922 A1    Aug. 9, 2007

Related U.S. Application Data

(63) Continuation of application No. PCT/CH2004/000361, filed on Jun. 15, 2004.

(51) Int. Cl.
G01B 5/30 (2006.01)

(52) U.S. Cl. ...................................................... 73/760

(58) Field of Classification Search ............ 73/760–856
See application file for complete search history.

(56) References Cited

U.S. PATENT DOCUMENTS

| 5,360,016 A | 11/1994 | Kovacevic et al. |
| 5,470,354 A | 11/1995 | Hershberger et al. |
| 2002/0029045 A1* | 3/2002 | Bonutti ..................... 606/86 |
| 2004/0102786 A1* | 5/2004 | Grundei ..................... 606/88 |
| 2005/0065533 A1* | 3/2005 | Magen et al. ............... 606/102 |
| 2006/0081063 A1* | 4/2006 | Neubauer et al. ........... 73/818 |
| 2006/0095135 A1* | 5/2006 | Kovacevic .................. 623/20.32 |

FOREIGN PATENT DOCUMENTS

| EP | 1 304 093 | 4/2003 |
| WO | WO 03/079940 | 10/2003 |

* cited by examiner

*Primary Examiner*—Max Noori
(74) *Attorney, Agent, or Firm*—Kay Kaplun & Marcin, LLP

(57) ABSTRACT

A probe used during a total knee arthroplasty for measuring forces and locations of their points of application and thereby moments includes two load sensitive plates t to be inserted in one joint-compartment of a knee joint each and each being provided with a top surface and a bottom surface. At least two load sensors may be situated on the top surfaces and/or the bottom surface of each load sensitive plate.

16 Claims, 2 Drawing Sheets

DEVICE FOR MEASURING TIBIO-FEMORAL FORCE AMPLITUDES AND FORCE LOCATIONS IN TOTAL KNEE ARTHROPLASTY

CROSS REFERENCE TO RELATED APPLICATION

This application is a continuation of International Patent Application No. PCT/CH2004/000361, filed Jun. 15, 2004, the entire contents of which is expressly incorporated herein by reference.

TECHNICAL FIELD

The present invention relates to a probe for measuring force amplitudes, locations and moments of force.

BACKGROUND OF THE INVENTION

During a Total Knee Arthroplasty (TKA), a surgeon needs to balance the collateral knee joint ligaments in order to ensure a stable artificial joint. Conventionally, the balance assessment is based on the surgeon's perception and experience by manually manipulating the knee joint. Assessing the ligament forces and moments acting in the knee "by hand" is subjective, and can lead to relatively large errors and repeatability problems.

In European document EP 1 304 093 by GOUGEON, a probe is used which allows the measurement of the compressive forces between each condyle of the femur and the tibial plateau. This probe comprises two load sensors, one for each condyle, and is attached to a plate-like support. A disadvantage of this probe is that it is not possible to determine the point of application of the compressive force. The moments which are important for ligament balancing remain unknown.

SUMMARY OF THE INVENTION

The present invention is to provide a remedy for the above-discussed disadvantages. It is an object of the invention to provide a probe that allows measuring the amplitude and location of the compressive force generated by each condyle. The present invention accomplishes the objective set out above with a probe used during a total knee arthroplasty for measuring force amplitudes and force locations comprising, a first and second load sensitive plate, each for insertion into a joint-compartment of a knee joint and each having a top surface and a bottom surface. The first and second load sensitive plates have adjoining inner lateral side walls and the plates are connected at the adjoining inner lateral side walls to each other. Also, the first and second load sensitive plates include at least two load sensors.

Advantages achieved by the invention are that the probe allows for measuring in real time the force amplitude and location separately for each condyle and therefore computing the moments acting on the knee joint to better assess the ligament balance; and keeping the patella at its anatomical place during the measurement, which is closer to the postoperative situation.

In one embodiment, the first and second load sensitive plates may comprise at least three load sensors, each non-colinearly arranged allowing measurement of the force amplitudes and locations with respect to two perpendicular axes, preferably one extending in a medio-lateral direction and the other one extending in a antero-posterior direction.

In another embodiment, the probe further comprises a tibial base plate, providing a fixed and defined reference surface for the probe.

In a further embodiment, the probe further comprises a set of wedges allowing a variation of the tibio-femoral gap according to the patient anatomy and ligament releasing procedure.

In another embodiment, each load sensor may comprise a bridge-shaped structure and at least one piezoresistive sensor attached thereto. The bridge-shaped structures may be configured such that each load sensor provides measurement at one discrete point. Preferably, the discrete point measurements of the load sensors are spaced apart relative to one another by a distance greater than 2 mm.

The measured parameters may be used as inputs to a computational biomechanical model of the knee joint acting as an assistive expert system.

In a further embodiment, instead of electrically connecting the load sensitive sensors with the data processing instrument, (e.g. the computer) by means of cables, wireless telemetry may be used to transmit the measurement signals of the load sensors to the data processing instrument, e.g. the computer. This has the advantage of improving the ergonomics of the probe, and the handling of the probe may be facilitated as well.

BRIEF DESCRIPTION OF THE DRAWINGS

The probe is explained in even greater detail in the following exemplary drawings. The probe may be better understood by reference to the following drawings, wherein like references numerals represent like elements. The drawings are merely exemplary to illustrate the structure, operation and method of use of the bone plate and certain features that may be used singularly or in combination with other features and the invention should not be limited to the embodiments shown.

DESCRIPTION OF THE PREFERRED EMBODIMENTS

Figure 1:
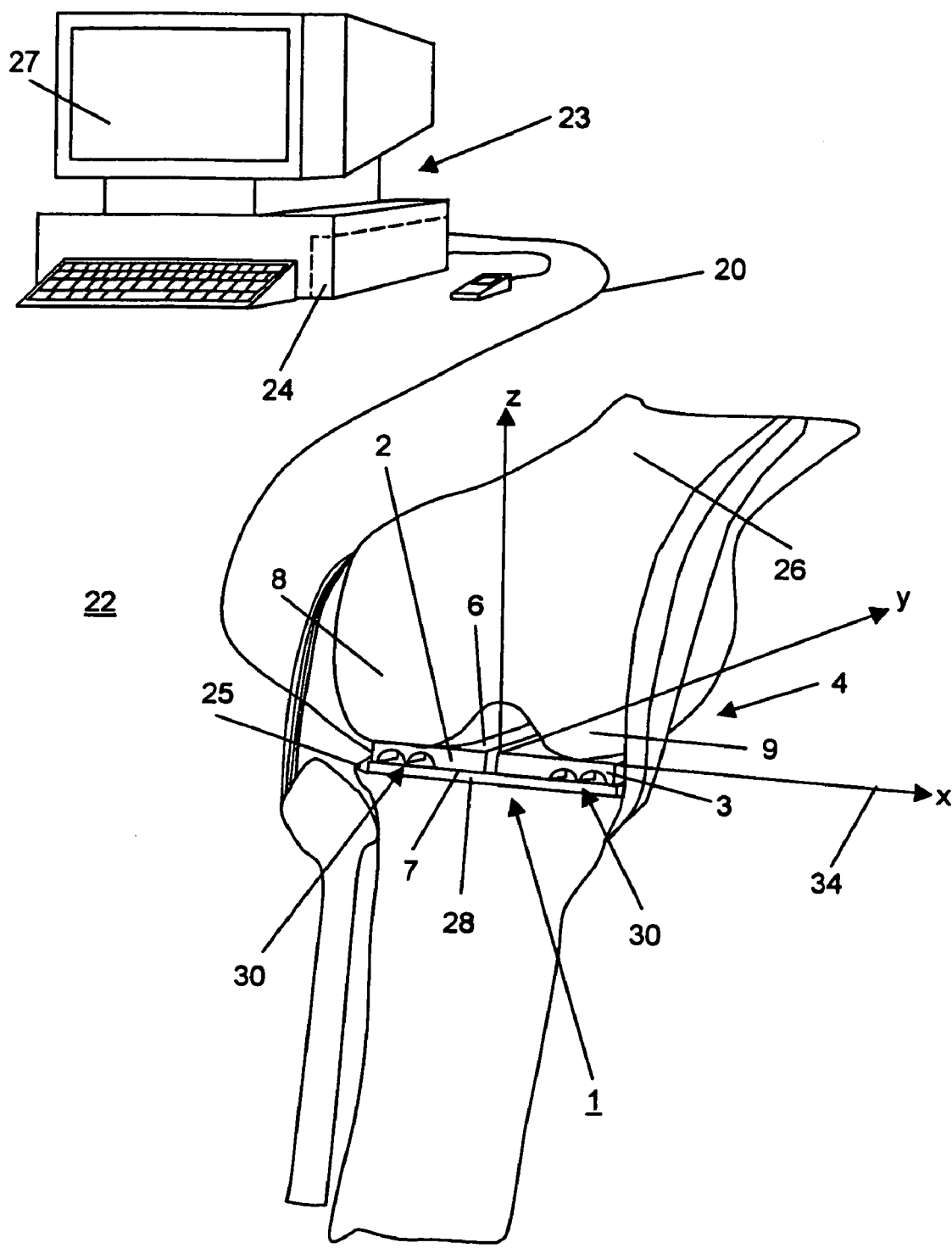
FIG. 1 a perspective view of a human knee joint with a probe inserted according to one embodiment of the invention and a computer.

FIG. 1 represents a measuring apparatus 22 comprising a probe 1 situated between the tibial plateau 25 and the two condyles 8, 9 of a human knee joint 4. The measuring apparatus 22 may also comprise a data acquisition and processing instrument 24 connected wirelessly or by means of cables 20 to the probe 1 and a computer 23. The probe 1 may comprise two load sensitive plates 2, 3, each having a top surface 6 and a bottom surface 7. The bottom surfaces 7 may be in contact with the top surface of a tibial base plate 28 lying on the tibial plateau 25 and each of the top surfaces 6 may be in contact with one condyle 8, 9 of the femur 26. Each load sensitive plate 2, 3 is situated in one knee-compartment and is subjected to the forces of each condyle 8, 9. The probe may further comprise a set of wedges allowing a variation of the tibio-femoral gap according to the patient anatomy and ligament releasing procedure.

Figure 2:
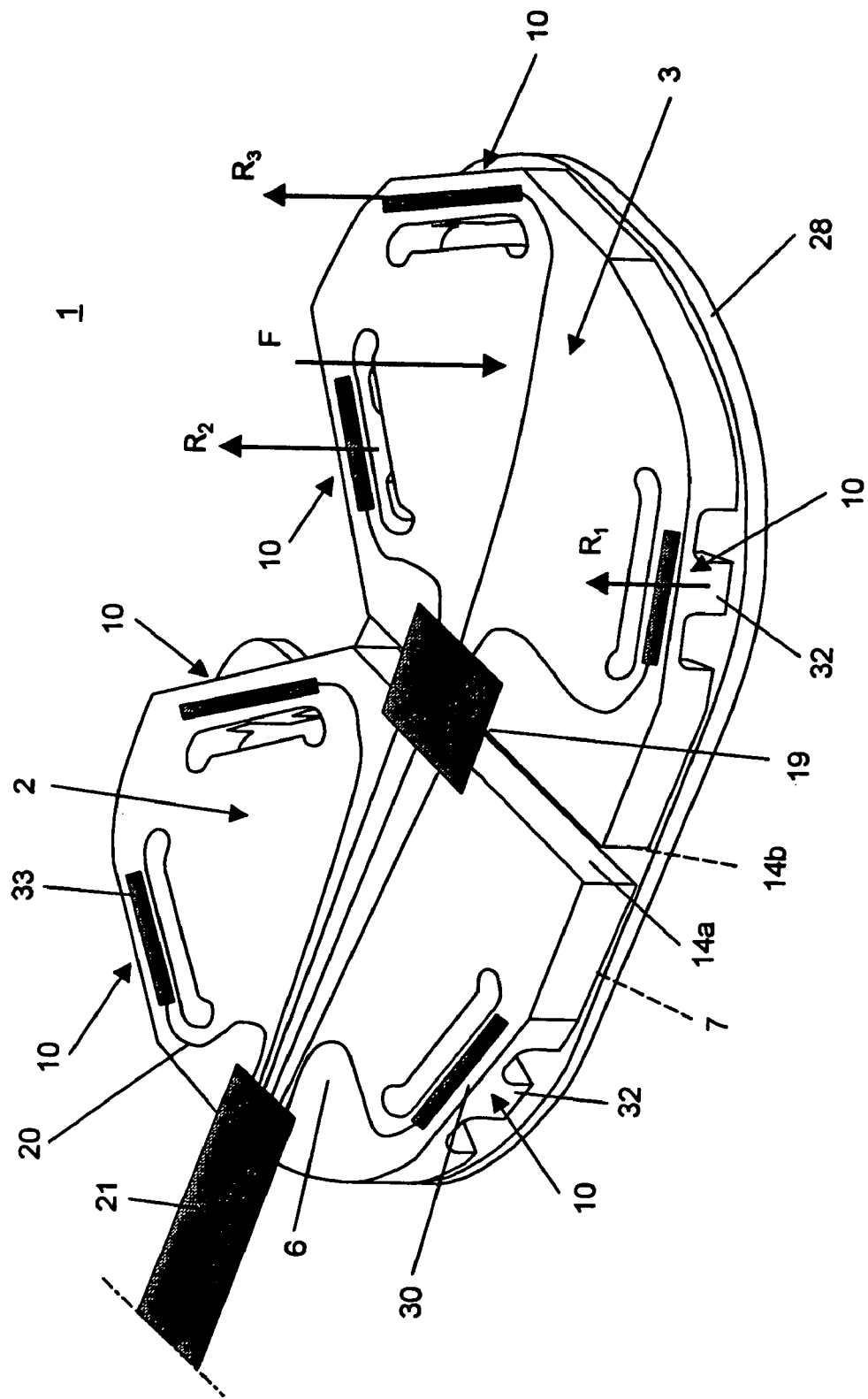
FIG. 2 a perspective view on the embodiment of the probe shown in FIG. 1.

FIG. 2 depicts a perspective view on an exemplary embodiment of the probe 1 comprising two load sensitive plates 2, 3 each for one condyle 8, 9 of a human knee joint 4. The two plates 2, 3 may have a polygon-like shape with rounded corners. The peripheries of the plates 2, 3 are configured preferably so that the shape of the probe 1 is adapted to the shape of the tibial plateau 25. Each load sensitive plate 2, 3 may have an inner lateral side wall, 14a, 14b, respectively. The first and second load sensitive plates 2, 3 may be connected at their adjoining inner lateral side walls 14a, 14b, allowing for easier insertion of the probe into the tibio-femoral gap. The connection between the plates 2, 3 may not extend the length of the adjoining inner lateral side walls 14a, 14b. Such a connection allows the tibio-femoral gap to be varied by means of the above wedges. Specifically, the two load sensitive plates 2, 3 may be connected to each other by means of a flexible joining element 19 attached at the top surfaces 6 next to adjoining inner lateral side walls 14a, 14b of the load sensitive plates 2, 3. Furthermore, there may be a gap between the two connected load sensitive plates 2, 3. Each plate 2, 3 may contain at least two, and preferably three load sensors 10 that are situated on the top surface 6, bottom surface 7, or in combination on both the top and bottom surfaces 6, 7 near the periphery of the plates 2, 3. In the exemplary embodiment shown in FIG. 2, the load sensors 10 are provided with cables 20 for measurement signal transmission that are combined to a cable form 21 near the periphery of the first or second load sensitive plate 2, 3 whereby each cable 20 is connected to the data acquisition and processing instrument 24 (FIG. 1). At a gap between the inner lateral side walls 14a, 14b, the cables 20 of the load sensors 10 situated on the first load sensitive plate 2 may be integrated in the flexible joining element 19. Instead of using cables 20 the measurement signals may be wirelessly transmitted. Wireless telemetry may be used to transmit the measurement signals of the load sensors to the data processing instrument, e.g. the computer. This has the advantage of improving the ergonomics of the probe, and the handling of the probe may be facilitated as well.

The load sensors, preferably at least three, may be non-colinearly arranged, allowing measurement of the force amplitudes and locations with respect to two perpendicular axes, preferably one extending in a medio-lateral direction and the other one extending in a antero-posterior direction. Each load sensor may comprise a bridge-shaped structure 30 (FIG. 2) elastically deformable with respect to the load applied onto the top surfaces 6 of the load sensitive plates 2, 3. The elastically deformable bridge-shaped structures 30 may be situated near the periphery of each plate 2, 3 and spaced apart from each other, whereby at least two of the bridge-shaped structures 30 are situated at an angle relative to each other.

The bridge-shaped structures 30 may include thick-film piezoresistive sensors 33 and provided with a central pillar 32 which is convexly, preferably spherically, shaped at the bottom. The piezoresistive sensors 33 sense an electric resistance change, depending on the force applied. Arranging the piezoresistive sensors 33 in a Wheatstone bridge allows converting the resistance change into an electric signal measurable by means of the data acquisition and processing instrument 24 (FIG. 1).

In particular, the bridge-shaped structures may be configured such that each load sensor provides measurement data for a discrete point. Preferably, the discrete point measurements of the load sensors are spaced apart relative to one another by a distance greater than 2 mm. The contact between the load sensitive plates 2, 3 and the tibial base plate 28 or the wedges (not shown) occurs at the bottom of the pillar center 32 of each bridge-shaped structure 30. In this way, three reaction forces $R_1$, $R_2$, $R_3$ orthogonal to the tibial base plate 28 are generated at the pillars 32 of the bridge-shaped structures 30 when a force F is applied on the respective load sensitive plate 2, 3. These reaction forces $R_1$, $R_2$, $R_3$ may be measured by the piezoresistive sensors 33. The measured parameters may be used as inputs to a computational biomechanical model of the knee joint acting as an assistive expert system. Specifically, the amplitude and location of the initial load F may be computed using equations of mechanical equilibrium. According to the measurement device 22 shown in FIG. 1 the amplitude and the location x, y within the reference system 34 of the compressive force on the probe 1 is generated by each condyle 8, 9 and may be computed by means of the computer 23 using the values of the electric signals measured by the data acquisition and processing instrument 24.

The surgeon may display the computed parameters, i.e., the amplitude and location of the compressive forces and the resulting moments, which characterize the degree of ligament force balance in real-time on monitor 27 of the computer. Relevant parameters may be computed during flexion/extension of the knee joint 4 (FIG. 1).

Description of the Surgical Procedure:

Following a standard opening of the knee joint 4, a tibial precut is performed in order to obtain a flat reference surface and enough room for the probe 1. The probe 1 is inserted into the knee joint 4 and the measuring system, as well as the computer 23, is prepared for the acquisition, processing and display of the measurements. The amplitude and location of the compressive contact force, as well as the moments of each femoral condyle 8, 9, are then measured in real-time at various knee flexion angles. The computer 23 displays the raw measurements and an interpretation of these measurements is based on a computational biomechanical model of the knee joint 4 which acts as an assistive expert system. The ligamentous balance is then corrected according to the measurements and to the biomechanical interpretation. The measurement and correction procedure is repeated until the ligaments are balanced. Finally, the probe 1 is removed and the prosthetic components are inserted. Alternatively, the probe 1 can be used after the insertion of the femoral and/or tibial prosthetic component.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A probe used during a total knee arthroplasty for measuring force amplitudes and force locations comprising:
   a first and second load sensitive plate, each for insertion into a joint-compartment of a knee joint and each having a top surface and a bottom surface,
   wherein each of the first and second load sensitive plates each include at least two load sensors, and wherein the first and second load sensitive plates have adjoining inner lateral side walls and are connected at the adjoining inner lateral side walls.

2. A probe according to claim 1, wherein at least two load sensors are situated on the top surface of the first load sensitive plate and at least two load sensors are situated on the top surface of the second load sensitive plate.

3. A probe according to claim 1, wherein at least two load sensors are situated on the bottom surface.

4. A probe according to claim 1, wherein at least one load sensor is situated on the top surface and at least one load sensor is situated on the bottom surface.

5. A probe according to claim 1, wherein the first and second load sensitive plate comprise at least three load sensors each that are noncolinearly arranged.

6. A probe according to claim 1, further comprising a base plate configured to be in contact with the tibia.

7. A probe according to claim 1, further comprising a set of wedges.

8. A probe according to claim 1, wherein each load sensor comprises a bridge-shaped structure and at least one piezoresistive sensor.

9. A probe according to claim 1, wherein measured parameters are used as inputs of a computational biomedical model of the knee joint acting as an assistive expert system.

10. A probe according to claim 1, wherein wireless telemetry is used to transmit measurement signals emitted by the load sensors to a computer.

11. A probe according to claim 1, wherein each load sensor provides measurement data for a discrete point.

12. A probe according to claim 11, wherein the discrete point measurements of the load sensors are spaced apart relative to one another by a distance greater than 2 mm.

13. A probe according to claim 1, wherein connection between the first and second load sensitive plates is via a flexible joining element.

14. A probe according to claim 13, wherein there is a gap between the connected first and second load sensitive plates.

15. A probe according to claim 13, wherein connection between the first and second load sensitive plates is along a segment of the adjoining inner lateral side walls.

16. A method of using a probe during a total knee arthroplasty on a knee joint for measuring force amplitudes and force locations comprising the steps of:
   a. performing a tibial precut to obtain a flat reference surface and space for the probe, the probe comprising first and second load sensitive plates connected at adjoining lateral side walls and including at least two load sensors;
   b. inserting the probe into the knee joint;
   c. measuring in real time amplitude and location of compressive contact force as well as moments of each femoral condyle at various knee flexion angles;
   d. displaying the compressing contact forces and moments on a display;
   e. interpreting the compressing contact forces and moments based on a computational biomechanical model of the knee joint;
   f. correcting ligamentous balance according to the interpretation;
   g. repeating steps (c) through (f) until ligaments are balanced; and
   h. removing the probe and inserting prosthetic components.

\* \* \* \* \*